United States Patent [19]

Shoher et al.

[11] Patent Number: 4,957,439
[45] Date of Patent: Sep. 18, 1990

[54] PREFABRICATED DENTAL PONTIC, PONTIC CONNECTOR AND ASSEMBLY

[76] Inventors: Itzhak Shoher, 50 Shlomo-Hamelech St., Tel-Aviv, Israel, 64386; Aharon E. Whiteman, 13 J.L. Perez St., Petach-Tikvah, Israel, 49206

[21] Appl. No.: 97,824

[22] Filed: Sep. 17, 1987

[51] Int. Cl.$^5$ ............................................. A61C 13/12
[52] U.S. Cl. ........................................ 433/180; 433/181
[58] Field of Search ............... 433/180, 181, 182, 183, 433/9, 218, 223

[56] References Cited

U.S. PATENT DOCUMENTS

| | | | |
|---|---|---|---|
| 318,581 | 5/1885 | Sheffield | 433/183 |
| 2,411,001 | 11/1946 | Rothkranz | 433/182 |
| 3,423,827 | 1/1969 | Bahm et al. | 433/183 |
| 4,704,089 | 11/1987 | Shoher et al. | 433/183 |
| 4,713,005 | 12/1987 | Marshall et al. | 433/180 |

FOREIGN PATENT DOCUMENTS

| | | | |
|---|---|---|---|
| 3537253 | 4/1987 | Fed. Rep. of Germany | 433/171 |
| 0899433 | 5/1945 | France . | |

*Primary Examiner*—Gene Mancene
*Assistant Examiner*—Adriene B. Lepiane
*Attorney, Agent, or Firm*—E. Lieberstein

[57] ABSTRACT

The prefabricated dental pontic of the present invention comprises a metal body having a mesiodistal dimension shorter than the span between the abutment teeth separating an edentulous space to be filled with the pontic and an arm extending from each opposite end of the metal body with each arm having a trough-like channel. A pontic connector is preferably used to mount each arm to a retaining member mounted on each abutment tooth.

11 Claims, 3 Drawing Sheets

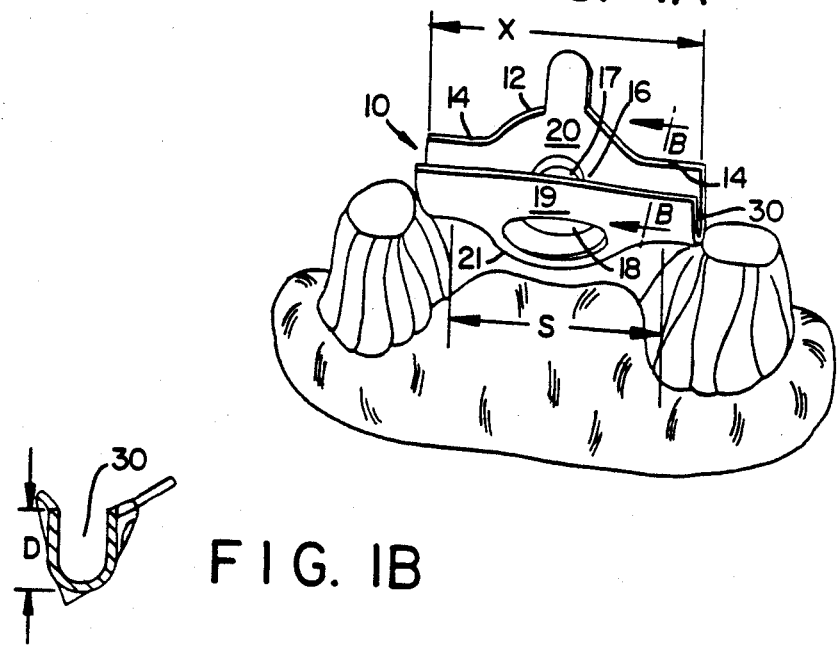
FIG. 1A
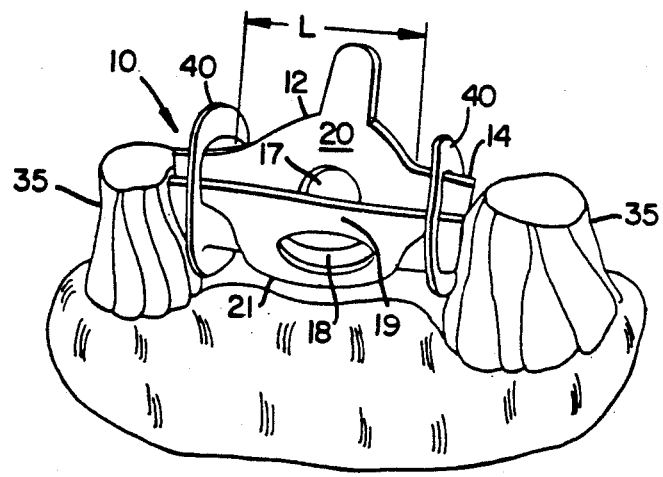
FIG. 1B
FIG. 3

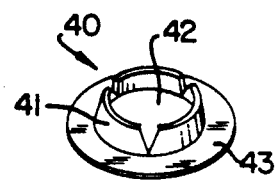
FIG. 2
FIG. 4
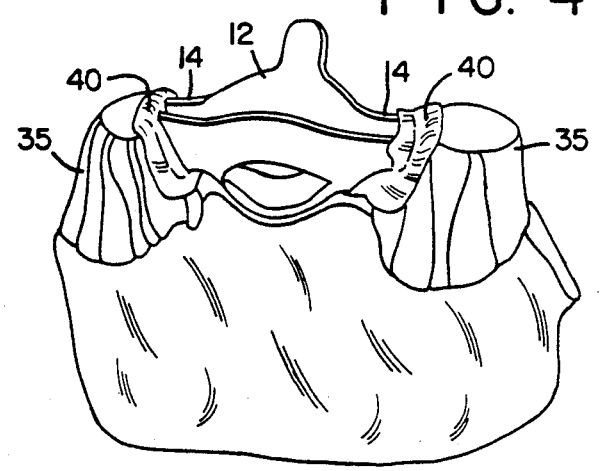
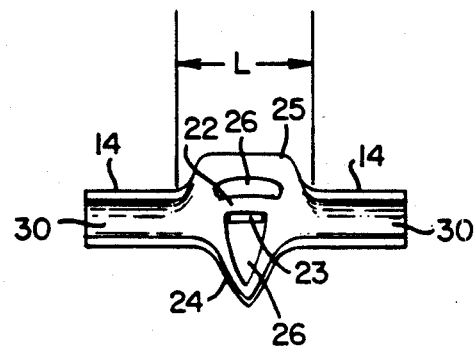
FIG. 5
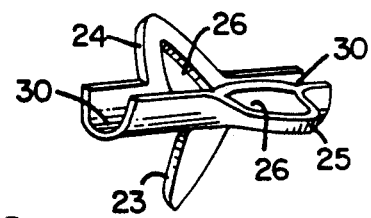
FIG. 6

PREFABRICATED DENTAL PONTIC, PONTIC CONNECTOR AND ASSEMBLY

BACKGROUND OF THE INVENTION

1. Field of the Invention

The present invention relates to a prefabricated dental pontic, a connector for a pontic, and an assembly for forming a dental bridge.

2. Description of the Prior Art

Crown and bridge prosthodontics is the science and art of the complete restoration of one or more teeth and the replacement of one or more natural teeth with an artificial device. A bridge is used to replace at least one missing tooth and is supported by natural teeth. A bridge which is not cast in one piece includes a pontic which fills the edentulous space and a connector which connects the pontic to a retaining member such as a crown formed on an abutment tooth adjacent the pontic. In the conventional bridge, the pontic is joined to the retainer by means of a solder joint which forms the connector.

The primary purpose of the dental bridge is to receive the forces of occlusion and to transmit them through the abutments so that occlusion is restored to the patient, thereby contribution to mastication. The bridge should also augment the ability of the patient to enunciate and maintain the positions of the opposing teeth. The present day construction of a dental bridge is a time consuming, involved and complex process which requires the application of many independent procedures including the following: waxing, spruing, investing, casting, cleaning, trimming, cutting and stoning. The process, as conventionally practiced, is referred to colloquially as the "lost wax casting method" and, at present, is the universally accepted procedure for making a bridge. In following this procedure, not only is it time consuming, but each step must be meticulously followed with the dental technician paying strict attention to detail to assure accuracy of the cast product and proper fit. It is also difficult to make any adjustments to a cast bridge to compensate for errors.

Construction a bridge from a prefabricated pontic offers the advantage of speed, simplicity, and substantial cost savings over the cast bridge. Although many previous attempts have been made to construct prefabricated pontic assemblies for fabricating a non-preparatory bridge to metal retainers, such prior art constructions have either been too unwieldly for practical use or were unable to provide a proximal joint of sufficient strength to permit the bridge to meet acceptable clinical standards. The proximal joint formed heretofore between a metal retainer and a pontic using solder was known to be weak.

SUMMARY OF THE INVENTION

The prefabricated pontic of the present invention eliminates waxing, spruing, investing and casting. The pontic is joined to abutment teeth preferably using the pontic connector of the present invention to form a proximal joint which is comparable in strength to the joint of a cast bridge. Moreover, the pontic of the present invention is easily fitted and adjusted into proper alignment between the abutment teeth.

The prefabricated pontic of the present invention is adapted to join metal retaining member(s) mounted upon abutment teeth separating an edentulous space in the fabrication of a bridge, and comprises a metal body having a mesiodistal dimension shorter than the span between the abutment teeth and an arm extending from each opposite end of the metal body, having a trough-like channel for placement between the metal body and the retaining members.

The pontic connector of the present invention connects a prefabricated pontic having an arm extending from each opposite end thereof to a retaining member on an abutment tooth or teeth for forming a solder joint therebetween in the fabrication of a bridge, and comprises means for mounting the connector to the arm of the pontic at a location adjacent the abutment tooth, and a thin metal member projecting from said mounting means with said metal member being pliable and adjustable for adaptation to a surface of the retaining member so as to hold the pontic in an aligned position relative to the retaining member in preparation for soldering and for reinforcing the solder joint formed at the attachment of the arm to the retaining member.

The present invention is also directed to an assembly for fabricating a dental bridge between metal retainers mounted on abutment teeth separating an edentulous space comprising; a prefabricated pontic having a metal body with a mesiodistal dimension shorter than the span between the abutment teeth, and an arm having a trough-like channel extending from each opposite end adjacent the abutment teeth, and means for connecting each arm to a metal retainer at the interproximal in preparation for soldering.

BRIEF DESCRIPTION OF THE DRAWINGS

Other advantages of the present invention will become apparent from the following detailed description of the invention when read in conjunction with the following drawings of which:

FIG. 1A is a side elevation of a prefabricated pontic in accordance with the present invention in preparation for placement between metal retainers in a working model of two abutment teeth representative of a canine and premolar;

FIG. 1B is an end view in cross-section of the prefabricated pontic of FIG. 1A taken along the lines 1B—1B thereof;

FIG. 2 is a view in perspective of the pontic connector of the present invention;

FIG. 3 is a side elevation of the prefabricated pontic of FIG. 1A shown fitted in position abutting the adjacent retaining members with the pontic connector of FIG. 2 mounted on each of the arm of the pontic;

FIG. 4 shows the arrangement of FIG. 3 in side elevation with each of the pontic connectors adapted to the retaining members on a working model for fabricating a three-unit bridge;

FIG. 5 is a view in perspective of a preferred anterior prefabricated pontic in accordance with the present invention;

FIG. 6 is an end perspective view of the pontic of FIG. 5; and

DETAILED DESCRIPTION OF THE INVENTION

Figure 7:
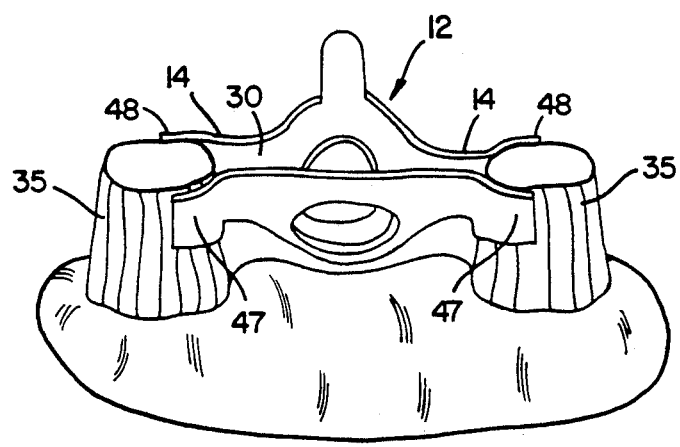
FIG. 7 is a side elevation of an alternate embodiment of a prefabricated pontic of the present invention shown in position between two retaining members in a working model for a three-unit bridge.

The prefabricated pontic of the present invention is identified in the drawings of FIG. 1A, 3, 4, 5 and 7, respectively, with the reference numeral 10 and may be used in the preparation of either a molar or anterior restoration. In each case, the pontic (10) comprises a metal body (12) and an arm (14) extending from each opposite end of the metal body (12). The pontic (10) may be fabricated from any desired metal or from a metal alloy composition, although the selection of the metal or metal alloy should meet the standards of compatibility for use in the oral cavity. Accordingly, the pontic should preferably include gold as at least one of its constituent elements. In addition, any conventional manufacturing method may be used to prefabricate the pontic (10), including conventional die casting and metal stamping.

The metal body (12) may be shaped into any design or configuration and may be a solid mass of metal or have open spaces. Moreover, the geometrical shape of the metal body (12) may vary considerably, based upon whether a molar or anterior restoration is involved. Although the geometry of the pontic metal body (12) is not critical to the present invention, it is preferred that the configuration of the metal body for a posterior restoration form a cradle-like geometry as shown in FIGS. 1, 3 and 4 in accordance with the principles of construction taught and described in U.S. Pat. No. 4,231,740, the disclosure of which is herein incorporated by reference. The cradle-like geometrical structure should have a large, occlusal concavity (16). The metal body (12) should also have relatively large, open spaces (17) and (18) in the wing-like arms (19) and (20), which extend outwardly toward the buccal and lingual surfaces of the restoration. The open spaces provide an open metal framework. The underside (21) of the body (12) may loop occluso-gingivally to form an arch. The length ("L") of the metal body (12) must be shorter mesiodistally than the span ("S") between the abutment teeth.

The preferred metal body design for an anterior restoration, as shown in FIGS. 5 and 6, may follow the general teachings of U.S. Pat. No. 4,318,697, the disclosure of which is herein incorporated by reference. The primary difference in design between the posterior and anterior design is the addition of an occlusal brace (22) which extends substantially upright directed to the occlusal, and a depending blade-like extension (23) which is directed gingivally. A pair of wing-like arms (24) and (25) extend outwardly toward the buccal and lingual surfaces of the restoration with open spaces (26) to form an open metal framework having a concave geometry. Although the anterior tooth is smaller in dimension than a posterior tooth, it is essential to the present invention that the length of the metal body (12) for both the anterior and posterior pontic be shorter mesiodistally than the span ("S") between the abutment teeth, so as to provide space for the arms (14) of the pontic (10) in the fabrication of a bridge, as will be explained in greater detail hereafter.

The arms (14) of the pontic (10) are preferably symmetrical and of the same uniform dimension in thickness, although such symmetry and equivalent dimensional thickness is not necessary. It is, however, an essential element of the present invention that the arms (14) form a trough-like channel (30). The trough-like channel (30) should preferably be "U-shaped," although a "V-shape" or box-shape with an open top would functionally serve the same purpose. In this regard, any geometry which would provide a reasonably deep depression (30) occluso-gingivally would be acceptable. The depth ("D") of the trough-like channel (30) depends on the restoration, but should in general have a depth greater than 0.5 mm, and generally between 0.5 mm to 2 mm deep, and with 1 mm to 1.5 mm being optimum.

The pontic (10) should be prefabricated with an arm length (X) which is intentionally longer than is required to fit the pontic between the abutment teeth so that the pontic arms may be shortened to accommodate for differences in spacing ("S") between any two abutment teeth. Accordingly, the length of each arm (14) on each side of the metal body (12) may be shortened to accurately fit the pontic into relatively tight engagement between the abutment teeth. Each arm (14) may be of any length, with the only requirement that it be long enough to form the trough-like channel (30).

Each arm (14) of the pontic (10) should be relatively rigid to provide a strong attachment to the adjacent metal retaining members (35). Each retaining member (35) may represent any type metal retainer, either full or partial, that is cemented to an abutment tooth for retaining a bridge. The metal retaining members (35) are shown in the figures for purposes of illustration representing metal copings for constructing full crowns. The preferred metal-retaining member (35) is a prefabricated metal coping as described in U.S. Pat. Nos. 4,459,112 and 4,492,579. The coping, as described in the aforementioned patents, is formed from a thin metal foil of two or more layers of metal arranged in a prefolded configuration with a plurality of foldable sections, which are folded over in preparation for adapting the coping to a die of the preferred tooth to be restored. The coping is then adapted to the die and heat treated.

Once the pontic (10) is fitted into a secure position abutting the metal retainers (35), the arms (14) may be soldered to the metal retainers (35) to form a solder joint at the interpromixal. This will usually require a highly skilled technician to form a sufficiently strong solder joint.

A prefabricated metal connector (40), as shown in FIGS. 2, 3 and 4, is preferably used to hold the parts together and in alignment for conducting a soldering operation. The metal connector (40) also reinforces the solder joint formed at the point of attachment with the retaining members (35). The prefabricated metal connector (40) consists of a thin member (41) in the form of band having a hole (42) and a thin metal extension or rim (43) projecting from the band (41). The arm (14) is fitted through the hole (42). The rim (43) should be very pliable so that it is readily bent over and adapted to one or more surfaces of the adjacent metal retainer (35). Although an annular band (41) is preferable, the band need not cover a full 360 degrees. Alternatively, the band member (41) may represent any clip-on means for providing attachment to the arm (14). In like manner, the rim (43) may be of any geometrical shape. In fact, the rim (43) need only extend in one direction from the band (41). Moreover, the rim (43) may be irregular in shape so that it covers a greater occlusal surface area, particularly for a molar restoration. The hole (42) should accommodate the arm (14) and as such may be rounded or "U-shaped", to match the shape of the arm (14).

The connector (40), and more particularly the rim (43), should be composed of a soft metal material which makes the rim easily adaptable to the retainer. The composition of the material should also be compatible with its use in the oral cavity and as such should be of a nonoxidizing metal or metal alloy. Moreover, the connector (40) or only its rim (43) can be formed from a multilayer construction with one layer having a melting temperature higher than the melting temperature of the solder so that such layer will retain its integrity after soldering. As such, one layer of the connector (40) can be used as the solder material which upon application of a flame from a Bunsen burner or in a furnace will melt to form the solder joint.

FIG. 3 shows the pontic (10) of FIG. 1 with its arms (14) sized and fitted into position abutting the adjacent retainers (35) in the working model of the abutment teeth for fabricating a dental bridge. The connectors (40) are mounted about the arm (14) before the pontic (10) is fitted in place. The rim (43) of the connector (40) is then bent over using appropriate dental tools to adapt the connector (40) to one or more surfaces of the retaining member (35) as shown in FIG. 4. The prefabricated assembly is now ready to be soldered. A conventional soldering operation is performed using any dental solder at a soldering temperature of 1050° C. or higher. The connector (40) ca have one layer composed of a soldering composition as earlier explained. Additional solder may be added using a solder material of any desired shape, such as a strip or a "U-shaped" member to match the shape of the arm (14). The trough-like channel formed by the arm (14) permits the solder to collect, flow and fill into the depression, thereby forming a strong solder joint around the area where the arm (14) joins the retainer (35). The arm (14) is thus able to transfer the load to the retainer (35). The reinforced solder joint has been shown to be stronger than the retaining member (35).

An alternate embodiment in which a prefabricated connector is not used is shown in FIG. 7. The arms (14) are cut open at their ends to form a bifurcated pair of arm connectors (47) and (48), which are adapted to the buccal and lingual surfaces of the retainer (35). The trough-like channel in the arm (14) is still essential to form a bed for the solder.

Although the invention has been described in connection with the fabrication of three-unit bridge, it should be apparent that the invention is equally applicable to the fabrication of a two-unit cantilever bridge or a multiple-unit bridge using two or more pontics. For the cantilever bridge, one arm of the pontic may be removed. For a multiple-unit bridge, two pontics may be joined by connecting the arms to one another. The arms may be united by welding and/or soldering and may be dimensioned to permit one arm to nest into another.

What we claim is:

1. A prefabricated structure for forming a pontic for joining metal retainer(s) mounted on an abutment tooth or teeth adjacent an edentulous space to be filled with the pontic in the fabrication of a bridge comprising: a metal body having open spaces in said body and having a mesiodistal dimension shorter than the span between the abutment teeth separating the edentulous space and an arm extending from said metal body, said arm having a free end for engaging said metal retainer at the interproximal and a trough-like channel extending from said free end with said trough-like channel having a depth in the occluso-gingival direction greater than at least about 0.5 mm such that the trough-like channel formed by said arm permits solder to collect, flow and fill into the channel for forming a reinforced solder joint upon soldering said arm to said retainer.

2. A prefabricated pontic as defined in claim 1 wherein said metal body has an arm extending from each opposite end thereof and with each arm having a trough-like channel abutting each retainer.

3. A prefabricated pontic as defined in claim 2 wherein said trough-like channel has a depth occluso-gingivally of between about 0.5 and 2.0 mm.

4. A prefabricated pontic as defined in claim 3 wherein said trough-like channel has a depth occluso-gingivally of between about 1.0 and 1.5 mm.

5. A prefabricated pontic as defined in claim 3 wherein said trough-like channel is substantially "U-shaped".

6. A prefabricated pontic as defined in claim 5 wherein said metal body forms a concavity with wing-like arms extending to the buccal and lingual surfaces of the metal retainer.

7. A prefabricated pontic as defined in claim 6 wherein said metal body further comprises an upright brace member and a depending section extending gingivally.

8. A prefabricated pontic as defined in claim 5 further comprising arm connectors extending from the trough-like channel of each arm for engaging the buccal and lingual surfaces of the metal retainer.

9. An assembly for fabricating a dental bridge between metal retainer(s) mounted on an abutment tooth or teeth separating an edentulous space comprising a prefabricated structure for forming a pontic having a metal body with a mesiodistal dimension shorter than the span between the abutment teeth and an arm extending from said metal body with said arm having a free end for engaging said metal retainer at the interproximal and having a trough-like channel extending from its free end with an occluso-gingival depth of at least about 0.5 mm so that the trough-like channel formed by said arm permits solder to collect, flow and fill into the channel to form a reinforced solder joint at the interproximal and means for connecting said arm to the adjacent metal retainer in preparation for soldering said arm to said retainer with said means having a ring-like configuration and an opening through which the free end of the arm is placed.

10. An assembly, as defined in claim 9, wherein said connecting means comprises a thin metal band with a pliable section adapted to be fitted over the metal retainer.

11. An assembly, as defined in claim 10, wherein said thin metal band has a projecting rim adapted to be bent over one or more surfaces of the retainer.

* * * * *